(12) United States Patent
Kashiwagi

(10) Patent No.: US 7,566,172 B2
(45) Date of Patent: Jul. 28, 2009

(54) RADIATION IMAGE TAKING APPARATUS HAVING INCLINING MEANS THAT INCLINES A FOCUSING GRID

(75) Inventor: Nobuhiko Kashiwagi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 115 days.

(21) Appl. No.: 11/865,490

(22) Filed: Oct. 1, 2007

(65) Prior Publication Data
US 2008/0080674 A1    Apr. 3, 2008

(30) Foreign Application Priority Data
Sep. 29, 2006    (JP)    ............... 2006-269371

(51) Int. Cl.
*G21K 1/10*    (2006.01)
*A61B 6/08*    (2006.01)
(52) U.S. Cl. ...................... 378/205; 378/155
(58) Field of Classification Search ............. 378/21, 378/22, 23, 24, 25, 26, 27, 37, 151, 154, 378/155, 205
See application file for complete search history.

(56) References Cited

U.S. PATENT DOCUMENTS

| | | | | |
|---|---|---|---|---|
| 5,241,578 A | * | 8/1993 | MacMahon | 378/154 |
| 5,357,554 A | * | 10/1994 | Schneiderman et al. | 378/155 |
| 5,388,143 A | * | 2/1995 | MacMahon | 378/206 |
| 5,517,546 A | * | 5/1996 | Schmidt | 378/206 |
| 5,949,850 A | * | 9/1999 | Tang | 378/154 |
| 6,502,984 B2 | * | 1/2003 | Ogura et al. | 378/206 |
| 6,510,202 B2 | * | 1/2003 | Tamura et al. | 378/155 |
| 6,702,459 B2 | * | 3/2004 | Barnes et al. | 378/197 |
| 6,782,077 B2 | * | 8/2004 | Hirai | 378/155 |
| 6,795,528 B2 | * | 9/2004 | Nokita | 378/155 |
| 6,890,099 B2 | * | 5/2005 | Tanaka et al. | 378/205 |
| 6,893,157 B2 | * | 5/2005 | Arakawa | 378/205 |
| 7,019,300 B2 | | 3/2006 | Watanabe | |
| 7,123,684 B2 | * | 10/2006 | Jing et al. | 378/37 |

FOREIGN PATENT DOCUMENTS

JP    2004-177251 A    6/2004

\* cited by examiner

*Primary Examiner*—Allen C. Ho
(74) *Attorney, Agent, or Firm*—Sughrue Mion, PLLC

(57) ABSTRACT

There is provided a radiation image taking apparatus having: a radiation source for irradiating an object; a radiation image detector; a focusing grid provided between the radiation source and the radiation image detector and consisting of radiation-transparent and opaque areas that alternate in a direction parallel to the radiation-receiving plane of the radiation image detector; a moving means that moves the radiation source in such a direction that the perpendicular from the radiation source to the focusing grid crosses the borderline between a radiation-transparent area in the focusing grid and the adjacent radiation-opaque area; and an inclining means that inclines the focusing grid in such a way that the focus of the focusing grid is brought into agreement with the radiation source that has been moved by the moving means.

5 Claims, 7 Drawing Sheets

(A)

(B)

(C)

RADIATION IMAGE TAKING APPARATUS HAVING INCLINING MEANS THAT INCLINES A FOCUSING GRID

The entire contents of documents cited in this specification are incorporated herein by reference

BACKGROUND OF THE INVENTION

The present invention relates to the technical field of taking/recording radiation image using a focusing grid, in particular, to a radiation imaging apparatus that enables an appropriate radiation image to be obtained even if a radiation source is moved.

In breast cancer screening, the success rate of early detection that is achieved through physical examination by inspection and palpation only is improved if it is combined with mammography by a radiation image taking apparatus solely intended for breasts (which is hereinafter referred to as a breast imaging apparatus); hence, breast cancer screening that is currently practiced involves the use of a breast imaging apparatus in addition to (or in place of) inspection and palpation.

The breast imaging apparatus comprises an imaging table enclosing a radiation image recording medium (which is hereinafter referred to as an imaging medium); to operate it, the breast is placed on the imaging table, compressed with a press plate, irradiated with a radiation from the press plate side; the radiation transmitted through the breast is received by the imaging medium and its radiation image is taken on the imaging medium.

The breast is composed of mammary gland tissue, fatty tissue, skin, etc. and in order to take a picture of the breast required for correct diagnosis, it is necessary that the breast be compressed to the highest possible uniformity in thickness to enable the imaging of the mammary gland and the fatty tissue in detail. In addition, in order to record a sharp image, it is preferred that the source of radiation be positioned right above the compressed breast so that an incoming radiation is normal to the breast.

A problem with the taking of radiation image is that scattered rays (scattered X-rays) will inevitably occur due, typically, to the tissue of an object such as the breast. If such scattered rays get into the detector, deterioration of image quality such as lower contrast will occur.

Under the circumstances, a radiation image taking apparatus such as a breast imaging apparatus is usually provided with a grid (a scattered rays removing grid) just in front of the detector (or its radiation-receiving plane) in order to block the entrance of scattered rays into the detector so that they will not cause deterioration of image quality (see, in particular, JP 2004-177251 A).

In one example, the grid consists of a lead plate or other radiation-opaque material that alternates with a similar plate form of a radiation-transparent material in a direction perpendicular to the length of each plate; in the case of a breast imaging apparatus, the two materials are arranged such that they alternate in the transverse direction of the subject (parallel to her chest wall).

The grid is also known to be available in two types, one being a parallel grid in which the radiation-transparent areas are formed parallel to each other and the other being a focusing grid (refer to FIG. 6) in which the radiation-transparent areas diverge progressively in the direction of radiation transmission so that the focus of convergence will coincide with the radiation source (the focus of X-rays).

SUMMARY OF THE INVENTION

As is well known, the operating mechanism of the breast imaging apparatus for taking a radiation image of the breast is such that a radiation that has passed through a compressed breast is allowed to be incident on a radiation image detector (a radiation image recording/taking medium) such as a radiation image converting panel (so-called IP) that utilizes a stimulable phosphor or a FPD (flat panel detector).

In addition, during image taking, the radiation source is preferably positioned right above the breast so that an incoming radiation is normal to the breast.

The breast imaging apparatus sometimes requires that the radiation source be moved, as in the case where it cannot otherwise be positioned right above the breast.

If the prior art apparatus using the above-described focusing grid is operated with the radiation source being moved, the focus of the grid will be offset from the radiation source, causing considerable decrease in the transmittance of the radiation or its selectivity (how much of direct X-rays can be selected from its mixture with scattered rays).

An objective of the present invention is to solve the aforementioned problems of the prior art and provide a radiation image taking apparatus such as a breast's radiation image taking apparatus that employs a focusing grid and which is capable of moving a radiation source for image taking, characterized in that even if the radiation source is moved, a radiation image of the breast can be obtained advantageously without lowering the transmittance and selectivity of the radiation.

In order to attain this objective, the present invention provides a radiation image taking apparatus comprising a radiation source for irradiating an object, a radiation image detector having a radiation-receiving plane that receives the radiation from the radiation source through the object for detecting a radiation image of the object, a focusing grid for removing the scattered rays of the radiation that is incident on the radiation image detector, the grid being provided between the radiation source and the radiation image detector and consisting of radiation-transparent and opaque areas that alternate in a direction parallel to the radiation-receiving plane of the radiation image detector, a moving means that moves the radiation source in such a direction that the perpendicular from the radiation source to the focusing grid crosses the borderline between a radiation-transparent area in the focusing grid and the adjacent radiation-opaque area, and an inclining means that inclines the focusing grid in such a way that the focus of the focusing grid is brought into agreement with the radiation source that has been moved by the moving means or that the line connecting the focus of the focusing grid and the radiation source that has been moved by the moving means crosses the focusing grid at right angles.

In the above-described radiation image taking apparatus of the present invention, the inclining means is preferably such that it inclines the focusing grid with respect to the radiation-receiving plane of the radiation image detector; in another preferred embodiment, the focusing grid is such that the radiation-transparent and opaque areas in the form of lines alternate in a direction that crosses the lines at right angles and the moving means moves the radiation source in the direction in which the radiation-transparent and opaque areas alternate; in yet another preferred embodiment, the radiation image taking apparatus has a grid moving means which causes the focusing grid to move in such a direction that the perpendicular from the radiation source to the focusing grid crosses the borderline between a radiation-transparent area in the focusing grid and the adjacent radiation-opaque area, and the inclining means inclines the focusing grid using the grid moving means; the inclining means inclines the focusing grid with part of it serving as the center of rotation.

According to the present invention having the structural design described above, when imaging is performed using the focusing grid with the radiation source being moved from the center of the grid, the focusing grid may be so inclined that the focus of the focusing grid is brought into agreement or substantial agreement with the radiation source (the focus of the radiation).

Hence, according to the present invention, when a breast's radiation image taking apparatus is operated to perform imaging with the radiation source being moved, as in the case where it is moved to position the radiation source right above the breast, an advantageous radiation image can be obtained consistently without suffering a drop in the transmittance or selectivity of the radiation.

DETAILED DESCRIPTION OF THE INVENTION

On the pages that follow, the radiation image taking/recording apparatus of the present invention is described in detail with reference to the preferred embodiments shown in the accompanying drawings.

Figure 1:
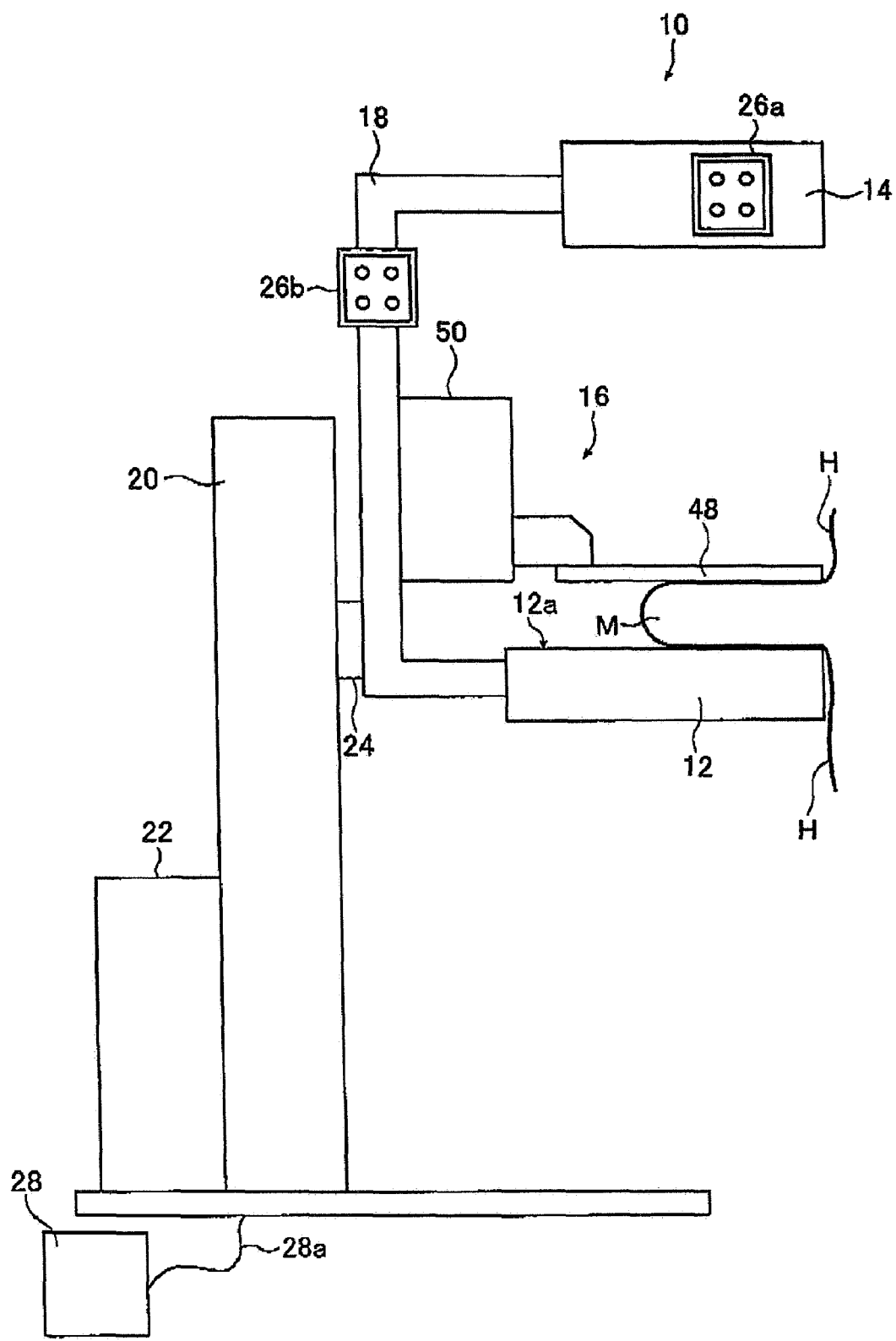
FIG. 1 shows in concept an example of the radiation image taking apparatus of the present invention.

FIG. 1 shows in concept an example of the radiation image taking apparatus of the present invention, in which it is applied as a breast's radiation image taking apparatus.

As FIG. 1 shows, the breast's radiation image taking apparatus which is generally indicated at 10 (and hereinafter referred to as a mammographic unit 10) is basically composed of an imaging table 12, an irradiating section 14, a compressing means 16, an arm 18, a base 20, and an X-ray irradiating high-voltage power supply 22. The illustrated mammographic unit 10 is basically the same as the ordinary breast's radiation image taking apparatus, except that it has two additional means described later in detail, one for moving radiation source 30 and the other for inclining scatter removing grid 54. In FIG. 1 and other drawings, the symbols M and H represent in concept the breast and chest wall, respectively.

In the illustrated mammographic unit 10, arm 18 is bent at right angles in two positions to assume a generally C-shaped form; the upper end of arm 18 is fixed to irradiating section 14 and the lower end to imaging table 12, with compressing means 16 fixed between irradiating section 14 and imaging table 12.

Figure 2:
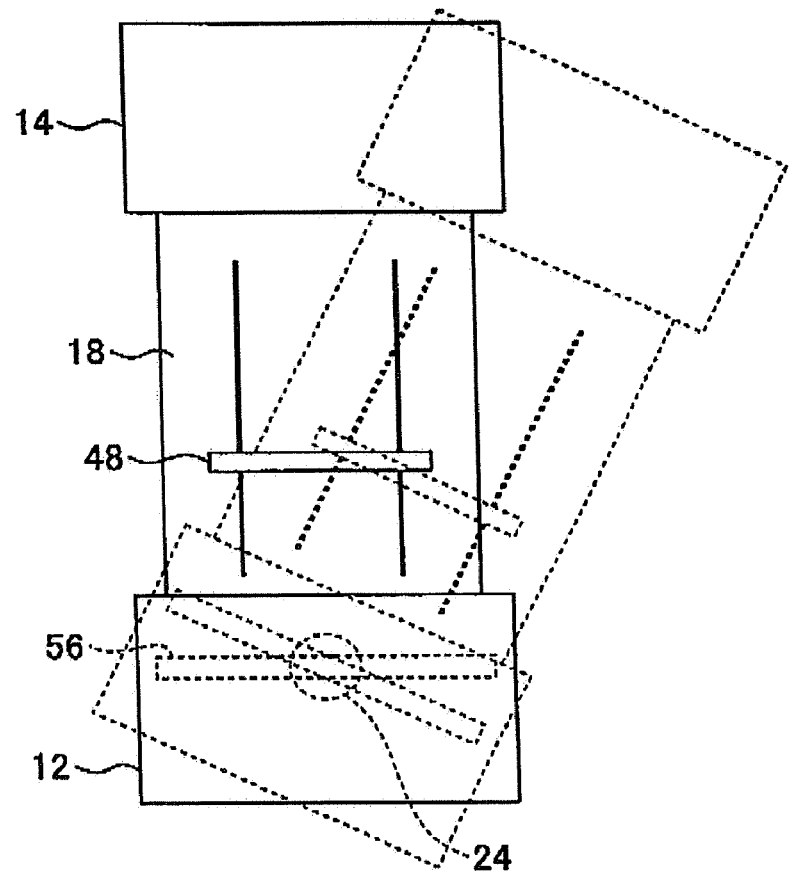
FIG. 2 shows in concept how the radiation image taking apparatus shown in FIG. 1 works.

Arm 18 is supported on base 20 by means of a shaft 24. Built in the interior of base 20 are a means for rotating shaft 24, as well as a means for vertically moving it. Arm 18 and, hence, imaging table 12 and irradiating section 14 are moved up and down as shaft 24 is moved up and down by the means that causes it to move vertically; in addition, as shown schematically in FIG. 2, they are rotated as shaft 24 is rotated by the means that causes it to rotate, whereupon angular adjustment is done to allow for MLO imaging and the like.

Base 20 is fitted with manipulating means 26 (26a and 26b), as well as a manipulating means 28 for making a variety of manipulations such as vertically moving and rotating arm 18 (or shaft 24).

Manipulating means 26a is fitted on a lateral side of irradiating section 14 and manipulating means 26b on a lateral side of arm 18: each of these manipulating means has switches associated with the rotation and vertical movement of arm 18, a switch that turns on a lamp for illuminating the field of irradiation, and other necessary switches. Manipulating means 28 is a pedal that is connected to base 20 via a cable 28a and has a switch associated with the vertical movement of a compressing plate 48 to be described later, a switch associated with the vertical movement of arm 18, and other necessary switches.

The transverse movement of radiation source 30 which will be described later is also achieved by manipulating means 26.

Figure 3:
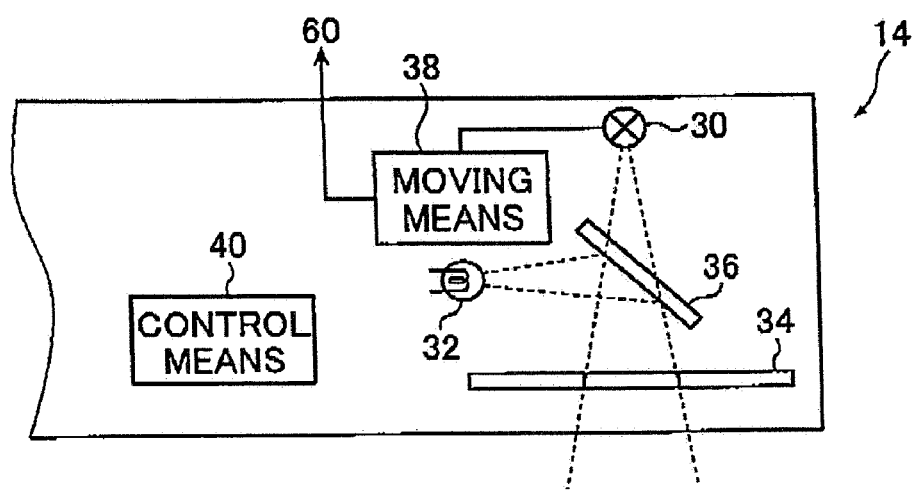
FIG. 3 shows in concept the irradiating section of the radiation image taking apparatus shown in FIG. 1.

Irradiating section 14 is a site for applying a radiation to breast M and, as shown schematically in FIG. 3, it has radiation source 30, a projected light source 32, a collimator 34 that regulates the field of irradiation, a mirror 36, and a means 38 for moving radiation source 30.

Irradiating section 14 is also provided with an apparatus control means 40 that manages and controls the overall operation of mammographic unit 10.

Radiation source 30 may be an ordinary radiation source that is conventionally used in radiation image taking apparatuses. Projected light source 32 is also a known light source that is used to illuminate the field of irradiation in radiation image taking apparatuses.

Mirror 36 transmits the radiation from radiation source 30 but reflects the light from projected light source 32.

In the illustrated case, radiation source 30 and projected light source 32 are provided in optically equivalent positions; to be more specific, radiation source 30 and projected light source 32 are arranged in such positions that when the optical path of the light from projected light source 32 is folded back at mirror 36, projected light source 32 coincides with radiation source 30; in other words, projected light source 32 lies on a straight line that optically connects radiation source 30 and a detector 56 to be described later.

Figure 4:
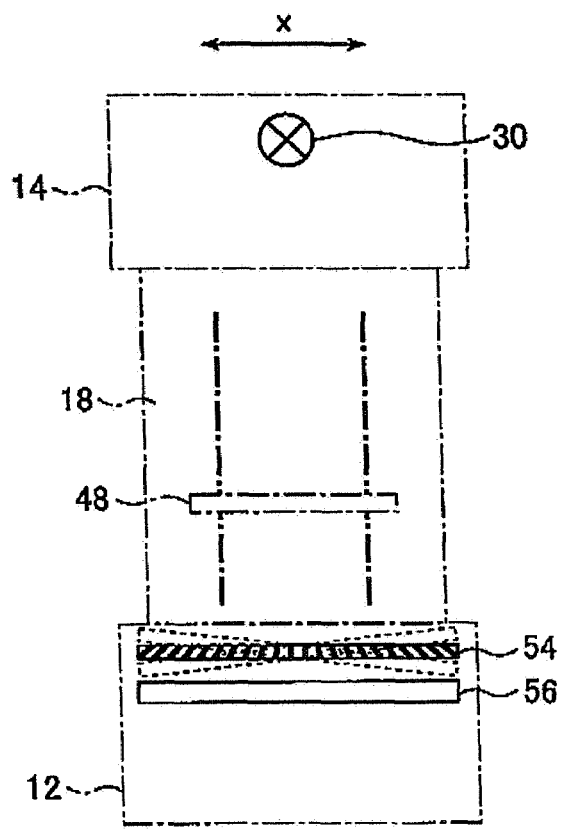
FIG. 4 shows in concept how the radiation image taking apparatus shown in FIG. 1 works.

Moving means 38, as shown conceptually in FIG. 4, moves radiation source 30 in a transverse direction indicated by a two-headed arrow x, that is from left to right and vice versa in a direction parallel to the chest wall of the subject who faces directly opposite mammographic unit 10; in FIG. 1, this direction is perpendicular to the paper. As will be described later in detail, the present invention is characterized in that when radiation source 30 is moved, scatter removing grid 54 provided within imaging table 12 to be described later is inclined as indicated by dashed lines in FIG. 4.

In the present invention, means 38 for moving radiation source 30 may be any of the known means for moving the radiation source that are utilized in a breasts radiation image taking apparatus and various other radiation image taking apparatuses. Moving means 38, if it has moved radiation source 30 in the transverse direction in response to a command entered by manipulating means 26, sends the information about the direction of movement (either right or left) and the amount of movement to a means 60 for inclining imaging table 12 which is described later.

Note that the amount of movement of radiation source 30 is not limited in any particular way and if the position of radiation source 30 which is yet to be moved is taken as the reference, it may be moved by a distance of up to about 3 to 30 cm either to the left or right as calculated from that reference position.

In mammographic unit 10, radiation source 30 is thus adapted to be movable and, as already mentioned, typically in the case where breast M cannot be positioned right under radiation source 30 if it remains in its reference position, radiation source 30 can be moved to the position right above breast M so that a radiation is incident normal to breast M, thus enabling the taking/recording of a sharp image of breast M.

The transverse movement of radiation source 30 may be exemplified by a transverse movement parallel to breast-holding plane 12*a* of imaging table 12 (i.e., the surface of detector 56 on which a radiation is incident) and a transverse movement as the result of rotation of radiation source 30 (which is hereinafter referred to as rotational movement for the sake of convenience) about the point at which the perpendicular from radiation source 30 to scatter removing grid 54 crosses the same grid 54 (or a point in the vicinity of that crossing point on the perpendicular); whichever of the two lateral movements may be performed.

In the illustrated mammographic unit 10, radiation source 30 is assumed to make a transverse movement parallel to breast-holding plane 12*a*.

Compressing means 16 compresses the breast onto imaging table 12 while its view is taken; compressing means 16 has a compressing plate 48 that compresses the breast onto imaging table 12 and a means 50 for vertically moving compressing plate 48. Compressing plate 48 is detachably mounted on vertically moving means 50 and available in two sizes, typically 18×24 cm for a breast of normal size and 24×30 cm for a larger breast.

In the illustrated mammographic unit 10, compressing plate 48 and vertically moving means 50 are basically of known types of a breast compressing plate and a means for vertically moving it that are provided in a known type of breast's radiation image taking apparatus.

Figure 5:
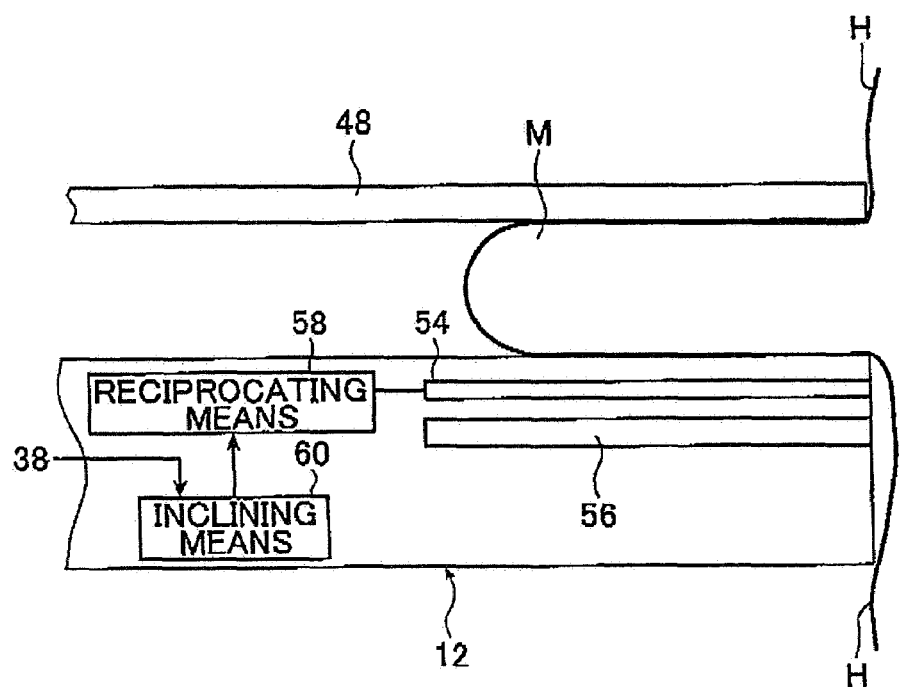
FIG. 5 shows in concept the imaging table of the radiation image taking apparatus shown in FIG. 1.

Imaging table 12 is a hollow case with its upper surface serving as breast-holding plane 12*a*; as shown schematically in FIG. 5, it contains scatter removing grid 54 (which is hereinafter referred to as grid 54), detector 56, a reciprocating means 58 that causes grid 54 to move in a Bucky motion, and inclining means 60 that inclines grid 54 as radiation source 30 makes the above-defined transverse movement.

Although not shown, imaging table 12 contains in it an AEC (automatic exposure control) sensor for measuring the radiation that has passed through the breast during pre-irradiation which is performed prior to the taking of a breast's radiation image for determining the imaging conditions.

Grid 54 is a scattered ray removing means (scattered ray removing grid) that consists of alternating radiation-transparent and opaque areas and which serves to remove the scattered rays (scattered X-rays) that have been generated by the breast's tissue and the like.

Figure 6:
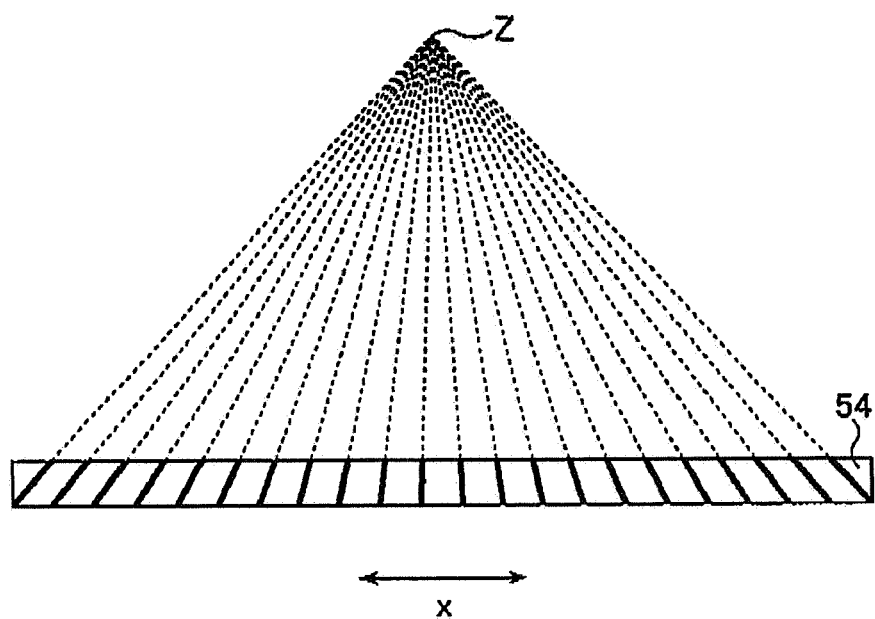
FIG. 6 shows in concept the focusing grid used in the radiation image taking apparatus shown in FIG. 1.

In the present invention, grid 54, as shown schematically in FIG. 6, is a focusing grid in which the radiation-transparent areas are designed to converge at focus Z in a direction opposite the travel of the radiation, viz, they diverge in the direction of travel of the radiation). It should also be noted that focus Z of convergence from grid 54 is positioned at radiation source 30 (the focus of X-rays).

In the present invention, grid 54 itself may be of any known types of focusing grid that are employed in a variety of breast's radiation image taking apparatuses.

In the illustrated mammographic unit 10, grid 54 is a plate-like product that consists of a lead plate or other radiation-opaque material alternating with a similar plate form of a radiation-transparent material in a direction perpendicular to the length of each plate. In other words, grid 54 has such a structure that the radiation-transparent and opaque areas in the form of lines alternate in a direction that crosses the lines at right angles.

In mammographic unit 10, grid 54 is provided in such a way that the direction in which the radiation-transparent and opaque areas alternate coincides with the above-defined transverse direction as indicated by two-headed arrow x.

Thus, in mammographic unit 10, radiation source 30 is moved in a direction perpendicular to the length of the radiation-transparent and opaque areas of grid 54 in such a way it crosses the boundary between any radiation-transparent area and the adjacent radiation-opaque area at right angles.

Note that in the present invention, the grid is by no means limited to one that has the above-described linear radiation-transparent and opaque areas and various grid designs can be adopted as long as they are focusing grids.

An alternative grid is of such a structure that it has a two-dimensional grid pattern consisting of crossed, square radiation-opaque areas that are arranged to form open spaces that are filled with a radiation-transparent material.

If it is used, this alternative grid is positioned in such a way that the crossed radiation-opaque areas do not align with the above-defined transverse direction but that they preferably intersect with the transverse direction at an angle of 45 degrees.

Detector 56 is an imaging medium for taking a radiation image.

In the present invention, detector 56 that can be used is not limited in any particular way and various types of imaging medium (radiation image recording medium) that are employed in radiation image taking apparatuses may be used, as exemplified by the IP (imaging plate) which depends on a stimulable phosphor for radiation image conversion or the flat panel detector which depends on a solid-state detector, a TFT (thin-film transistor) or the like for radiation-to-image conversion (or photoelectric conversion).

If detector 56 is of a type that uses an IP, it also contains in it an IP reading means that applies exciting light to the IP and photoelectrically reads the photostimulated light that has been issued from the IP in response to the admission of the exciting light.

Reciprocating means 58 is a grid moving means that reciprocates (swings) grid 54 or causes it to make a so-called Bucky motion in order to prevent the occurrence of fixed non-irradiated areas on the radiation-receiving plane of detector 56. Note that the Bucky motion as referred to in the present invention is by no means limited to a reciprocating motion and it may be such that only one movement is made in one direction in the taking of one view.

A picture of the breast that is taken in mammography preferably covers areas that are the closest possible to the chest wall of the subject. Hence, in order to create no gap between the area to be viewed and the chest wall, mammographic unit 10 is operated to perform a Bucky motion in the transverse direction and, accordingly, grid 54 in the illustrated case which consists of alternating linear radiation-transparent and opaque areas is usually positioned in such a way that the direction in which the two areas alternate coincides with the transverse direction defined above, namely, the direction in which a Bucky motion is made.

In the illustrated mammographic unit 10, the Bucky motion itself may be an ordinary type of Bucky motion that is performed in known breast's radiation image taking apparatuses.

Therefore, reciprocating means 58 can also adopt various structural designs that are employed in various radiation image taking apparatuses.

Figure 7:
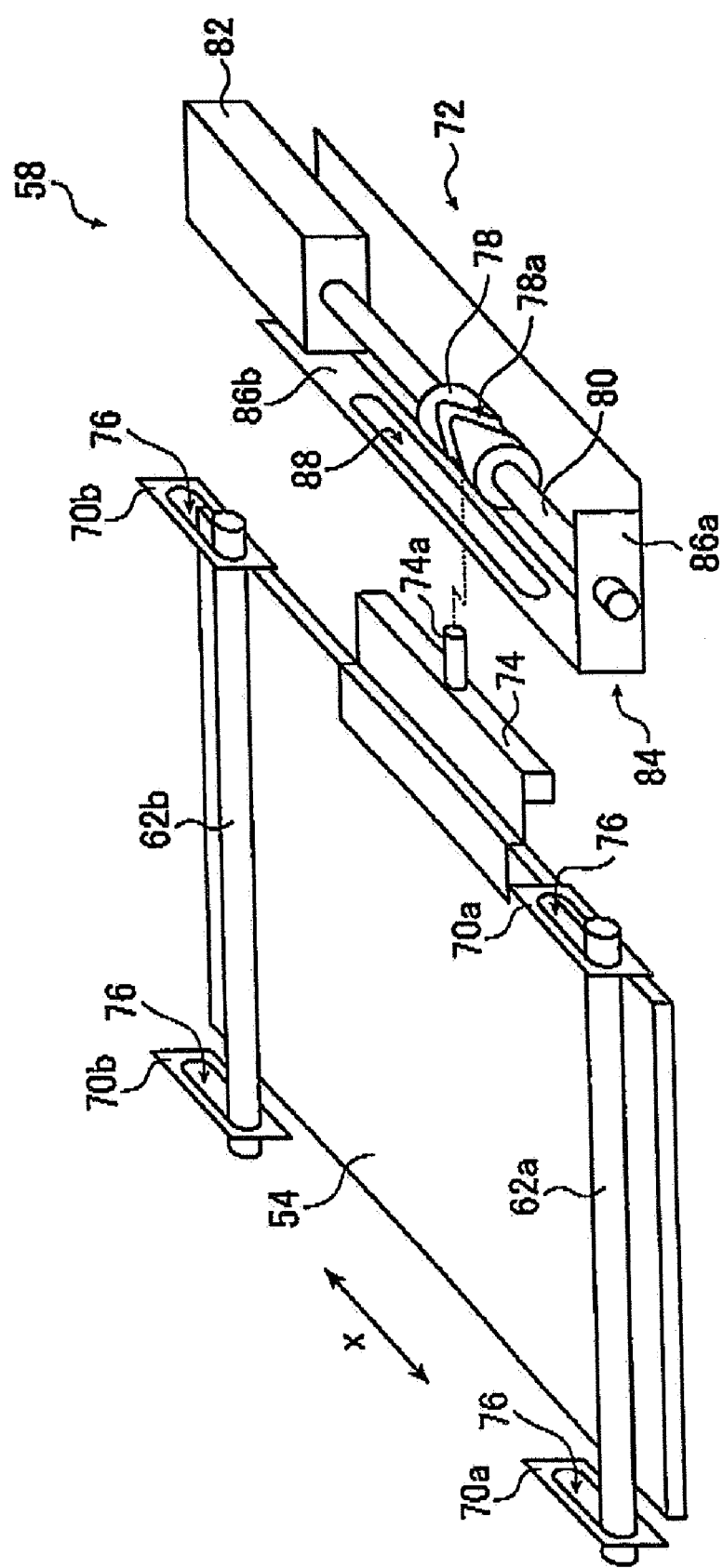
FIG. 7 is a diagrammatic perspective view of the reciprocating means which performs a Bucky motion in the radiation image taking apparatus shown in FIG. 1.

FIG. 7 is a diagrammatic view of reciprocating means 58 in the illustrated mammographic unit 10.

In the illustrated case, grid 54 has shafts 62 (62a and 62b) fixed near to opposite ends in the transverse direction (indicated by a two-headed arrow x) such that they extend in a direction perpendicular to that transverse direction (i.e., to have a longitudinal direction). In the following description, this direction perpendicular to the transverse direction, namely, the direction in which the distance from the chest wall of the subject facing directly opposite grid 54 increases/decreases along a perpendicular to her chest wall, is called a direction back and forth.

Reciprocating means 58 comprises those shafts 62, guide members 70 (70a and 70b) that guide shafts 62, a drive means 72, and an engaging member 74 that engages drive means 72 and grid 54.

Guide member 70 is a member in plate form that has slots 76 through which shafts 62 can be passed. In the illustrated case, two guide members 70a are provided in combination with two guide members 70b and that adds up to a total of four guide members 70. These guide members 70 are fixed in the vicinity of the four ends (corners) of grid 54 such that slots 76 extend in the transverse direction (indicated by two-headed arrow x) and guide members 70a get shaft 62a to be passed through slots 76 whereas guide members 70b get shaft 62b to be passed through slots 76.

Therefore, grid 54, being guided by those slots 76, reciprocates in the transverse direction to make a Bucky motion.

Drive means 72 comprises a cylindrical cam 78 that rotates about the center line through the cylinder, a rotating shaft 80 on cylindrical cam 78, a drive source 82 that causes cylindrical cam 78 to rotate, and a frame 84.

Cylindrical cam 78 is one that has a groove 78a formed in the lateral surface. Groove 78a is formed in such a way that it changes position along the longitudinal axis of the cylinder to form a continuous wavy line. In addition, cylindrical cam 78 is provided in such a way that the center line through the cylinder aligns with the transverse direction, in other words, groove 78a is so formed as to create a wavy line in the transverse direction.

Rotating shaft 80 on cylindrical cam 78 is rotatably supported at one end which engages drive source 82 whereas the other end is rotatably supported by frame 84. Frame 84 has a surface 86a that rotatably supports rotating shaft 80 and a rectangular surface 86b that is bent from surface 86a at right angles and extends in the transverse direction; the area of surface 86b that corresponds to cylindrical cam 78 is provided with a slot 88 that extends in the transverse direction.

Engaging means 74 secures grid 54 at an end in the direction back and forth, i.e., the end on the side which is distant from the subjects chest wall, and a rod-shaped portion 74a is fixed to it in a protrusive way in the direction back and forth.

As indicated by a dotted line in FIG. 7, this rod-shaped portion 74a is passed through slot 88 in frame 84 so that it is inserted into groove 78a in cylindrical cam 78. Consequently, by rotating cylindrical cam 78, engaging member 74 moves along groove 78a to reciprocate in the transverse direction, whereupon grid 54 is guided along slot 76 in guide member 70 to make a reciprocating or Bucky motion in the transverse direction.

As mentioned before, when radiation source 30 has been moved in the transverse direction, inclining means 60 inclines grid 54 in response to the information about the direction of movement and the amount of movement that has been supplied from moving means 38 for radiation source 30 provided in irradiating section 14, whereby the focus of grid 54 is brought into substantial agreement with radiation source 30 (the focus of the radiation).

In the illustrated case, inclining means 60, as shown conceptually in FIG. 8A, ascends guide member 70a of reciprocating means 58 which is to make a Bucky motion (i.e., brings it closer to radiation source 30) whereas it descends guide member 70b (if desired, guide member 70a may be allowed to descend and guide member 70b to ascend), whereby grid 54 is inclined as shown in FIG. 8B. Thus, in the embodiment under consideration, grid 54 is inclined by rotating it about the center in the transverse direction.

Note that guide members 70 may be allowed to ascend or descend by known means of moving members in plate form.

Figure 8:
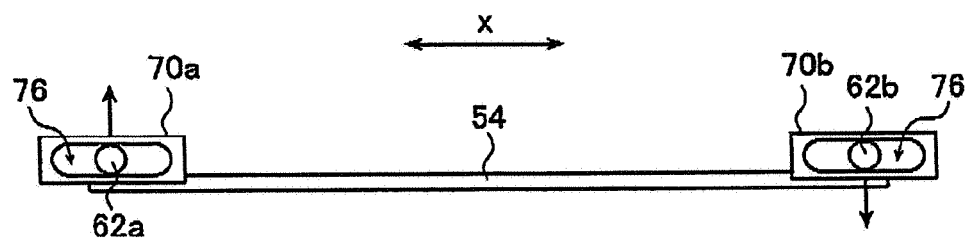
FIGS. 8A, 8B and 8C show in concept how the radiation image taking apparatus shown in FIG. 1 works.
Figure 8:
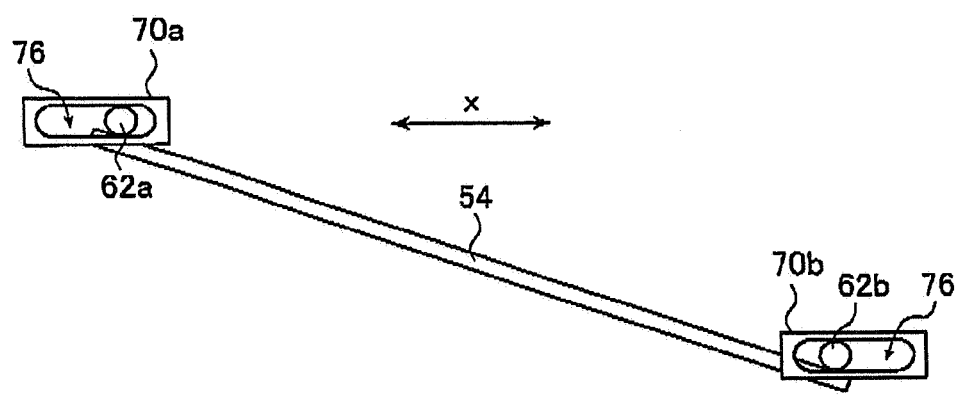
Figure 8:
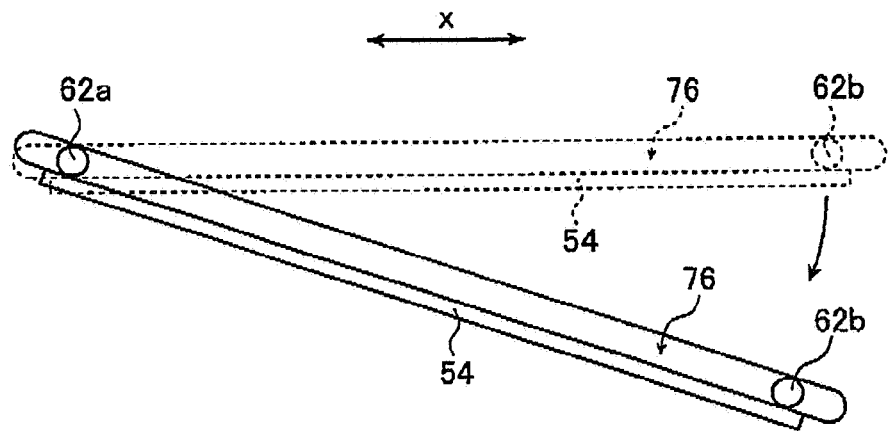

Note also that in the present invention, inclining means 60 for grid 54 is not limited to the means that ascend or descend guide members 70 as shown in FIG. 8 but various other means can be employed.

For example, in the cases shown in FIGS. 8 and 8B, grid 54 is inclined by ascending one pair of guide members 70 and descending the other pair. The present invention is by no means limited to these cases and grid 54 may be inclined by ascending or lowering only one pair of guide members 70.

In addition, the guide members for causing a Bucky motion need not be provided separated at opposite ends in the transverse direction and, as shown conceptually in FIG. 8C, they may be so provided as to extend through the entire region in the transverse direction; in this alternative case, the guide members may be inclined by rotating about an end of the guide members or grid 54 in the transverse direction (in the illustrated case, rotating about shaft 62a (which serves as the fulcrum)), whereupon grid 54 is inclined. Alternatively, the guide members may be inclined by rotating not about an end, but about the center, in the transverse direction of the guide members or grid 54. As mentioned before, shaft 62 is fixed to grid 54 to make an integral assembly and, what is more, the guide members are inclined together with grid 54 and, hence, as far as the inclining action of interest is concerned, shaft 62 and the guide members can be regarded as part of grid 54.

Thus, by setting the center of rotation in a portion of grid 54, as exemplified by its interior, its top surface (where a radiation is incident), a member that contacts the top surface, the bottom surface of grid 54, and a member that contacts the bottom surface, and by inclining grid 54 as if it swings, the space required to incline grid 54 can be minimized, thus preventing the size of imaging table 12 from becoming bulky. According to yet another approach that can be taken in the present invention, grid 54 is extended in a direction parallel to its plane and it may be inclined by pivoting it about a portion of the extended area (for examples of such portion, see above); this design is also effective in preventing the size of imaging table 12 from becoming bulky.

Alternatively, depending on the apparatus design, all members that are associated with grid 54 including the reciprocating means which is to perform a Bucky motion may be inclined as a whole, to thereby incline grid 54.

It should be noted here that in the illustrated mammographic unit 10, radiation source 30 moves in the transverse direction parallel to breast-holding plane 12a. This movement is hereinafter referred to as "parallel movement" for the sake of convenience.

Therefore, in mammographic unit 10, a mere inclination of grid 54 does not bring its focus into complete agreement with radiation source 30. Hence, in an apparatus like mammographic unit 10 where radiation source 30 makes a parallel movement, grid 54 is inclined as shown conceptually in FIG. 9, such that the line connecting focus z of grid 54 and radiation source 30 that has been moved in the transverse direction (the focus of the radiation) crosses grid 54 at right angles and this brings the focus of grid 54 into substantial agreement with radiation source 30.

Figure 9:
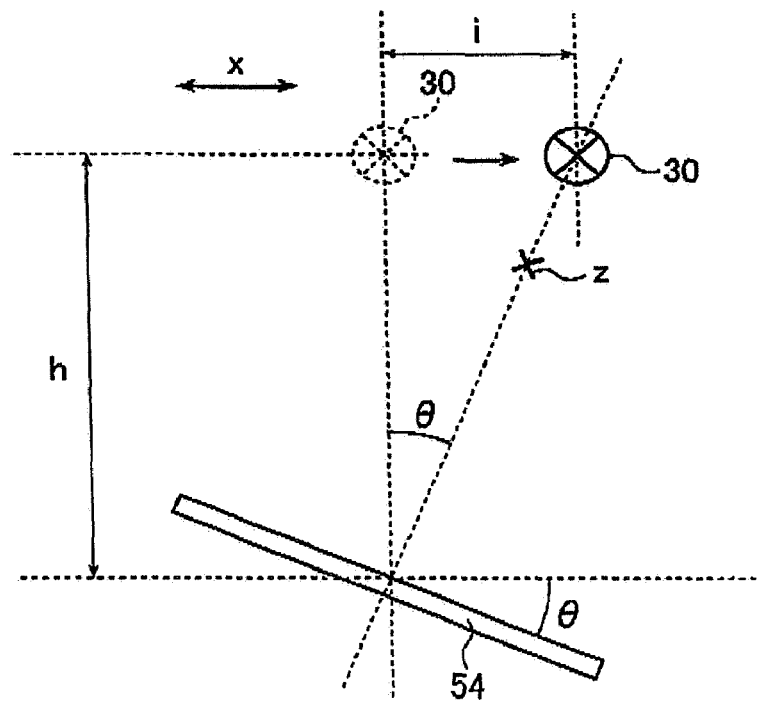
FIG. 9 shows in concept how the radiation image taking apparatus shown in FIG. 1 works.

To this end, as illustrated in FIG. 9, the angle of rotation θ that corresponds to the movement of radiation source 30 in the transverse direction is determined by the equation $\tan^{-1}(i/h)=\theta$ where i is the distance over which radiation source 30 has been moved in the transverse direction and h is the distance from the reference position of yet-to-be moved radiation source 30 to grid 54, and grid 54 is inclined through this angle θ, whereby the line connecting focus z of grid 54 and radiation source 30 that has been moved in the transverse direction is allowed to cross grid 54 at right angles.

Figure 10:
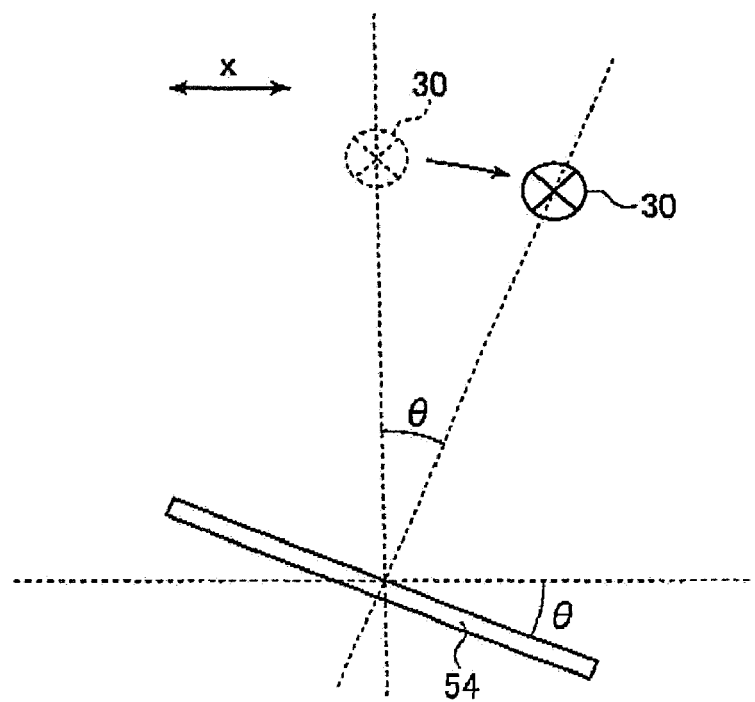
FIG. 10 shows in concept how the radiation image taking apparatus shown in FIG. 1 works according to another example.

It should be noted here that in the present invention, the movement of radiation source 30 in the transverse direction is not limited to the parallel movement defined above and, as shown conceptually in FIG. 10, radiation source 30 may be moved by rotating it about the point at which the perpendicular from radiation source 30 to grid 54 crosses grid 54.

In this alternative case, the angle of rotation θ that corresponds to the movement of radiation source 30 in the transverse direction is determined and grid 54 is inclined through this angle θ, whereby radiation source 30 that has been moved in the transverse direction can be brought into agreement with the focus of grid 54.

Here again, depending on the apparatus design, the center of rotation of radiation source 30 might not be located at the point at which grid 54 crosses the above-defined perpendicular but might come at a point in the vicinity of this crossing point that lies on that perpendicular. If this occurs, radiation source 30 cannot be brought into complete agreement with the focus of grid 54 but a slight offset is unavoidable. However, the amount of this offset may well be described as being within the range of an error and, hence, by inclining grid 54 through the angle of rotation θ of radiation source 30, the latter can be brought into agreement with the focus of grid 54.

Moving radiation source 30 transversely in the manner described above (in such a direction that the perpendicular from the radiation source crosses the radiation-transparent and opaque areas of grid 54) offers several advantages, one of which is that even if breast M cannot be placed right under radiation source 30 when it remains in its reference position, radiation source 30 can be moved to come right above breast M so that the incoming radiation is normal to the breast, thereby enabling the taking/recording of a sharp radiation image of breast M. Another advantage of moving radiation source 30 transversely is that even those areas of breast M which would otherwise become shadows when the radiation is incident normal to it can be properly imaged.

If radiation source 30 is moved transversely, the conventional apparatus that employs the focusing grid suffers the problem of a considerable drop in the transmittance and selectivity of radiation. In the present invention, however, the transverse movement of radiation source 30 is accompanied by a corresponding inclination of grid 54, whereby radiation source 30 is brought into complete or substantial agreement with the focus of grid 54; consequently, the decrease in the transmittance or selectivity of radiation that would otherwise result from the transverse movement of radiation source 30 can be prevented to ensure that an appropriate radiation image can be taken in a consistent manner.

On the following pages, the action of mammographic unit 10 is described.

First, compressing plate 48 of a size suitable for the size of breast M is fitted on vertically moving means 50.

In addition, depending on the need, the radiologist uses manipulating means 26 and the like to enter a command for moving radiation source 30 transversely. In response to the entry of this command, moving means 38 moves radiation source 30 and sends the information about the direction and distance of the movement to inclining means 60.

Having received the information about the direction and distance of the movement, inclining means 60 uses the supplied distance i and the preliminarily stored distance h between radiation source 30 and grid 54 to determine the angle of rotation θ that corresponds to the movement of radiation source 30 by means of the equation $\tan^{-1}(i/h)=\theta$. Then, in accordance with the direction of movement of radiation source 30, grid 54 is inclined by the determined angle θ until the line connecting focus z of grid 54 and radiation source 30 that has been moved transversely crosses grid 54 at right angles, whereupon focus z of grid 54 comes into substantial agreement with radiation source 30 (the focus of the radiation).

When the radiologist issues a command using manipulating means 28 and the like, vertically moving means 50 lowers compressing plate 48 to compress, for example, the right breast of the subject as it is held between imaging table 12 (or its breast-holding plane 12a) and compressing plate 48.

At the point in time when the compression of the right breast under compressing plate 48 has reached a predetermined state, radiation source 30 is driven to perform pre-irradiation. If pre-irradiation is performed, the imaging conditions (such as the tube voltage and the irradiation time) are set in accordance with the result of this pre-irradiation and the thickness of the breast (i.e., the height of compressing plate 48), and in accordance with the thus set imaging conditions, a radiation image of the right breast is taken and recorded on detector 56.

Even if radiation source 30 has been moved transversely in the process of taking the breast's picture, the present invention is so designed that grid 54 is accordingly inclined to bring radiation source 30 into substantial agreement with the focus of grid 54; as a result, an appropriate radiation image of the breast can be taken without suffering any drop in the transmittance and selectivity of the radiation.

While the radiation image taking apparatus of the present invention has been described above in detail, the present invention is by no means limited to the foregoing embodiments and various improvements and modifications can of course be made without departing from the scope and spirit of the present invention.

For instance, the foregoing embodiments relate to the preferred case of applying the present invention to a mammographic unit in which the effect of the present invention can be obtained easily or significantly; however, this is not the sole case of the present invention and it can be applied to a chest X-ray imaging apparatus and other apparatuses for taking/recording a radiation image.

It should also be noted that the direction in which the radiation source is to be moved is by no means limited to the transverse direction and it may be moved in any direction without particular limitation so long as it is such a direction that the perpendicular from the radiation source to the focusing grid crosses the boundary between radiation-transparent and opaque areas in the focusing grid.

What is claimed is:

1. A radiation image taking apparatus comprising:
   a radiation source for irradiating an object;
   a radiation image detector having a radiation-receiving plane that receives radiation from the radiation source through the object for detecting a radiation image of the object;
   a focusing grid for removing scattered rays of the radiation that is incident on the radiation image detector, the grid being provided between the radiation source and the radiation image detector and consisting of radiation-transparent and opaque areas that alternate in a direction parallel to the radiation-receiving plane of the radiation image detector;
   a moving means that moves the radiation source in such a direction that the perpendicular from the radiation source to the focusing grid crosses the borderline between a radiation-transparent area in the focusing grid and the adjacent radiation-opaque area; and
   an inclining means that inclines the focusing grid in such a way that a focus of the focusing grid is brought into agreement with the radiation source that has been moved by the moving means or that the line connecting the focus of the focusing grid and the radiation source that has been moved by the moving means crosses the focusing grid at right angles.

2. The radiation image taking apparatus according to claim 1, wherein the inclining means inclines the focusing grid with respect to the radiation-receiving plane of the radiation image detector.

3. The radiation image taking apparatus according to claim 1,
   wherein the focusing grid has the radiation-transparent and opaque areas in the form of lines alternating in a direction that crosses the lines at right angles, and
   wherein the moving means moves the radiation source in the direction in which the radiation-transparent and opaque areas alternate.

4. The radiation image taking apparatus according to claim 1, further comprising:
   a grid moving means which causes the focusing grid to move in such a direction that the perpendicular from the radiation source to the focusing grid crosses the borderline between a radiation-transparent area in the focusing grid and the adjacent radiation-opaque area, and
   wherein the inclining means inclines the focusing grid using the grid moving means.

5. The radiation image taking apparatus according to claim 1, wherein the inclining means inclines the focusing grid by rotating with part of it serving as the center of rotation.

* * * * *